US007553617B1

(12) United States Patent
Dower et al.

(10) Patent No.: US 7,553,617 B1
(45) Date of Patent: *Jun. 30, 2009

(54) PEPTIDE LIBRARY AND SCREENING SYSTEMS

(75) Inventors: William J. Dower, Menlo Park, CA (US); Steven E. Cwirla, Palo Alto, CA (US)

(73) Assignee: Affymax, Inc., Palo Alto, CA (US)

( * ) Notice: Subject to any disclaimer, the term of this patent is extended or adjusted under 35 U.S.C. 154(b) by 961 days.

This patent is subject to a terminal disclaimer.

(21) Appl. No.: 09/650,337

(22) Filed: Aug. 28, 2000

Related U.S. Application Data

(63) Continuation of application No. 09/261,731, filed on Mar. 3, 1999, now abandoned, which is a continuation of application No. 08/914,403, filed on Aug. 19, 1997, now abandoned, which is a continuation of application No. 07/541,108, filed on Jun. 20, 1990, now Pat. No. 5,723,286.

(51) Int. Cl.
*C12Q 1/70* (2006.01)
*C12Q 1/60* (2006.01)
*C12N 15/64* (2006.01)

(52) U.S. Cl. .............................. 435/5; 435/6; 435/69.1; 935/80; 935/81

(58) Field of Classification Search .................. 435/6, 435/69.1
See application file for complete search history.

(56) References Cited

U.S. PATENT DOCUMENTS

| 4,359,535 | A | 11/1982 | Pieczenik |
| 4,593,002 | A | 6/1986 | Dulbecco |
| 4,833,092 | A | 5/1989 | Geysen |
| 4,910,140 | A | 3/1990 | Dower |
| 5,096,815 | A | 3/1992 | Ladner et al. |
| 5,223,409 | A | 6/1993 | Ladner et al. |

FOREIGN PATENT DOCUMENTS

| GB | 2183661 | | 6/1987 |
| WO | WO 86/05803 | * | 6/1985 |
| WO | 87/01374 | | 3/1987 |
| WO | 88/05085 | | 7/1988 |
| WO | 88/06630 | | 9/1988 |
| WO | 89/06694 | | 7/1989 |
| WO | 90/02809 | | 3/1990 |
| WO | 90/05144 | | 5/1990 |
| WO | 90/14424 | | 11/1990 |
| WO | 90/14430 | | 11/1990 |
| WO | 90/14443 | | 11/1990 |
| WO | 91/17271 | | 11/1991 |
| WO | 91/18980 | | 12/1991 |
| WO | 92/01047 | | 1/1992 |
| WO | 92/07077 | | 4/1992 |
| WO | 92/09690 | | 6/1992 |
| WO | 92/15677 | | 9/1992 |
| WO | 92/15679 | | 9/1992 |

OTHER PUBLICATIONS

Seed et al. Molecular cloning of the CD2 antigen, the T-cell erythrocyte receptor, by a rapid immunoselection procedure, 1987, Proceedings of National Academy of Science of USA 84, pp. 3365-3369.*
Donegan et al. Isolation of a species-specific DNA probe for Neisseria gonorrhoeae using a novel technique particularly suitable for use with closely related species displaying high levels of DNA homology. Molecular Cell Probes Mar. 1989, vol. 3, No. 1, p. 13-26. Abstract only provided.*
Malik et al. Role of Capsid Structure and Membrane Protein Processing in Determining the Size and Copy Number of Peptides Displayed on the Major Coat Protein of Filamentous Bacteriophage. Journal of Molecular Biology 1996, vol. 260, p. 9-21.*
Ilyichev et al. Inserting foreign peptides into the major coat protein of bacteriophage M13, FEBS Letters, Apr. 27, 1992, vol. 301, No. 3, p. 322-324.*
Aruffo and Seed (1987), *Proc. Natl. Acad. Sci. USA* 84:8573-8577, "Molecular cloning of a CD28 cDNA by a high-efficiency COS cell expression system".
Barbas et al. (1991), *Proc. Natl. Acad. Sci. USA* 88:7978-7982, Assembly of combinatorial antibody libraries on phage surfaces: The gene III site.
Barrett et al. (1992), *Anal. Biochem.* 204:357-364, "Selective enrichment and characterization of high affinity ligands from collections of random peptides on filamentous phage".
Bass et al. (1990), *Proteins: Structure, Function, and Genetics* 8:309-31 4, "Hormonephage: An enrichment method for variant proteins with altered binding properties".
Better et al. (1988), *Science* 240:1041-1043, "*Escherichia coli* secretion of an active chimeric antibody fragment".
Boeke and Model (1982), *Proc. Natl. Acad. Sci. USA* 79:5200-5204, "A prokaryotic membrane anchor sequence: Carboxyl terminus of bacteriophage fi gene III protein retains it in the membrane".
Bottger (1988), *BioTechniques* 6:878-80, "High-efficiency generation of plasmid cDNA libraries using electro-transformation".
Cesareni (1992), *FEBS Letters* 307:66-70, "Peptide display on filamentous phage capsids".
Cwirla et al. (1990), *Proc. Natl. Acad. Sci. USA* 87:6378-6382, "Peptides on phage: A vast library of peptides for identifying ligands".

(Continued)

*Primary Examiner*—Bruce Campell
*Assistant Examiner*—Louise Humphrey
(74) *Attorney, Agent, or Firm*—Goodwin Procter, LLP

(57) ABSTRACT

Peptides which bind to selected receptor molecules are identified by screening libraries which encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule.

3 Claims, 4 Drawing Sheets

OTHER PUBLICATIONS de la Cruz et al. (1988), *J. Biol. Chem.* 263(9):4318-4322, "Immunogenicity and epitope mapping of foreign sequences via genetically engineered filamentous phage".

Devlin et al. (1990), *Science* 249:404-406, "Randon peptide libraries: A source of specific protein binding molecules".

Dower et al. (1988), *Nucl. Acids Res.* 16(13):6127-6145, "High efficiency transformation of *E. coli* by high voltage electroporation".

Felici et al. (1991), *J. Mol. Biol.* 222:301-310, "Selection of antibody ligands from a large library of oligopeptides expressed on a multivalent exposition vector".

Garrard et al. (1991), *Bio/Technology* 9:1373-1377, "FAB assembly and enrichment in a monovalent phage display system".

Geysen et al. (1987) *J. Immunol. Meth.* 102:259-274, "Strategies for epitope analysis using peptide synthesis".

Goldsmith and Konigsberg (1977), *Biochem.* 16(12):2686-2694, "Adsorption protein of the bacteriophage fd: Isolation, molecular properties, and location in the virus".

Greenwood et al. (1991), *J. Mol. Biol.* 220:821-827, "Multiple display of foreign peptides on filamentous bacteriophage".

Harlow et al. (1988). *Antibodies: A Laboratory Manual*, Cold Spring Laboratory Press, Cold Spring Harbor, NY, pp. 23-35, "Antibody antigen interactions".

Heery and Dunican (1989), *Nucl. Acids Res.* 17(19):8006, "Improved efficiency M13 cloning using electroporation".

Hoogenboom et al. (1991), *Nucl. Acids Res.* 19(15):4133-4137, "Multi-subunit proteins on the surface of filamentous phage: methodologies for displaying antibody (Fab) heavy and light chains".

Huse et al. (1989), *Science* 246:1275-1281, "Generation of a large combinatorial library of the immunoglobulin repertoire in phage lambda".

Il'ichev et al. (1990), *Molekulyarnaya Biologiya* 24:530-535, "M13 filamentous bacteriophage in protein engineering".

Jacobs et al. (1990), *Nucl. Acids Res.* 18(6):1653, "High-efficiency electro-transformation of *Escherichia coli* with DNA from ligation mixtures".

Kang et al. (1991), *Proc. Natl. Acad. Sci. USA* 88:4363-4366, "Linkage of recognition and replication funtions by assembling combinatorial antibody Fab libraries along phage surfaces".

McCafferty et al. (1990), *Nature* 348:552-555, "Phase antibodies: Filamentous phage displaying antibody variable domains".

Meo et al. (1983), *Proc. Natl. Acad. Sci. USA* 80:4084-4088, "Monoclonal antibody to the message sequence Tyr-Gly-Gly-Phe of opioid peptides exhibits the specificity requirements of mammalian opioid receptors".

Oliphant et al. (1986), *Gene* 44:177-183, "Cloning of random-sequence oligodeoxynucleotides".

Parmley and Smith (1988), *Gene* 73:305-318, "Antibody-selectable filamentous fd phage vectors: Affinity purification of target genes".

Parmley and Smith (1989), *Adv. Exp. Med. Biol.* 251:215-218, "Filamentous fusion phage cloning vectors for the study of epitopes and design of vaccines".

Scott et al. (1990), in *Advances in Gene Technology: The Molecular Biology of Immune Diseases and the Immune Response*, Streilein et al. (eds), IRL Press, New York, pp. 224, "An epitope library".

Scott and Smith (1990), *Science* 249:386-390, "Searching for peptide ligands with an epitope library".

Shigekawa and Dower (1988), *BioTechniques* 6(8):742-751, "Electroporation of eukaryotes and prokaryotes: A general approach to the introduction of macromolecules into cells".

Skerra and Pluckthun (1988), *Science* 240:1038-1041, "Assembly of a functional immunoglobulin Fv Fragment in *Escherichia coli*".

Smith et al. (1990), *J. Cell. Biochem.*, Supp. 14C:246, abst. CK319 (19th Ann. Mgt., UCLA Symp. Mol. Cell. Biol., Feb. 3 to Mar. 11), "An epitope library".

Smith (1985), *Science* 228:1315-1317, "Filamentous fusion phage: Novel expression vectors that display cloned antigens on the virion surface".

Ward et al. (1989), *Nature* 341:544-546, "Binding activities of a repertoire of single immunoglobulin variable domains secreted from *Escherichia coli*".

Wilson and Gough (1988), *Nucl. Acids Res.* 16(24):11820, "High voltage *E. coli* electro transformation with DNA following ligation".

Young and Davis (1983), *Science* 222:778-782, "Yeast RNA polymerase II genes: Isolation with antibody probes".

Zacher et al (1980), *Gene* 9:127-140, "A new filamentous phage cloning vector: fd-tet".

Y.S. Gho, et al., Development of Antiangiogenin Peptide Using a Phage-Displayed Peptide Library, vol. 57, Cancer Research, Sep. 1997, pp. 3733-3740.

* cited by examiner

| | | | | |
|---|---|---|---|---|
| YGGLGL | YGSLVL | YGALGG | YGWNGL | YGLWQS |
| YGGLGI | YGSLVQ | YGALSW | YGWWLT | YGFWGM |
| YGGLGR | YGSLVR | YGALDT | YGWLAT | YGKWSG |
| YGGLNV | YGSLAD | YGALEL | YGWANK | YGPFWS |
| YGGLRA | YGSLLS | | | YGEFVL |
| YGGLEM | YGSLNG | YGAIGF | YGWWTY | YGDFAF |
| | YGSLYE | | YGWFAD | |
| YGGIAS | | YGAWTR | YGWFPA | YAWGWG |
| YGGIAV | YGSWAS | | | YAGFAQ |
| YGGIRP | YGSWAS | | YGTFIL | |
| YGGIRP | YGSWQA | | YGTWST | YSMFKE |
| YGGWAG | YGSFLE | | YGVWAS | |
| YGGWGP | | | YGVWWR | |
| YGGWSS | | | | |
| YGGMKV | | | | |
| YGGFPD | | | | |

PEPTIDE LIBRARY AND SCREENING SYSTEMS

CROSS-REFERENCES TO RELATED APPLICATIONS

This application is a continuation of U.S. patent application Ser. No. 09/261,731, filed Mar. 3, 1999; which is a continuation of U.S. patent application Ser. No. 08/914,403, filed Aug. 19, 1997; which is a continuation of U.S. patent application Ser. No. 07/541,108, filed Jun. 20, 1990 and issued as U.S. Pat. No. 5,723,286. Each of the foregoing priority applications, inclusive of the disclosure, claims and amendments presented therein, is incorporated by reference herein in their entirety.

FIELD OF THE INVENTION

The present invention relates generally to methods for selecting peptide ligands to receptor molecules of interest and, more particularly, to methods for generating and screening large peptide libraries for peptides with desired binding characteristics.

BACKGROUND OF THE INVENTION

As molecular biology has helped to define regions of proteins that contribute to a particular biological activity, it has become desirable to synthesize short peptides to mimic (or inhibit) those activities. Many of the disadvantages encountered in therapeutic, diagnostic and industrial settings with purified proteins, or those produced by recombinant means, could easily be avoided by short synthetic peptides. For instance, synthetic peptides offer advantages of specificity, convenience of sample or bulk preparation, lower relative cost, high degree of purity, and long shelf-life.

Despite the great promise of synthetic peptides, the technology remains, to a large extent, a laboratory tool. Precise sequence and binding data are not available for most proteins of significant medical, agricultural or industrial interest. Even when the sequence of a protein is known, the process of identifying short sequences which are responsible for or contribute to a biological activity may be extremely tedious, if not nearly impossible in many instances.

Thus, the ability to generate and efficiently screen very large collections of peptides for desired binding activities would be of enormous interest. It would enable the identification of novel agonists and antagonists for receptors, the isolation of specific inhibitors of enzymes, provide probes for structural and functional analyses of binding sites of many proteins, and ligands for many other compounds employed in a wide variety of applications.

The generation of large numbers of peptide sequences by the cloning and expression of randomly-generated mixtures of oligonucleotides is possible in the appropriate recombinant vectors. See, e.g., Oliphant et al., Gene 44:177-183 (1986). Such a large number of compounds can be produced, however, that methods for efficient physical and genetic selection are required. Without such methods the usefulness of these large peptide libraries in providing ligands of potential interest may be lost. The present invention provides methods for efficient screening and selection from a large peptide library, fulfilling this and other related needs.

SUMMARY OF THE INVENTION

The present invention provides novel methods and compositions for identifying peptides which bind to preselected receptor molecules. The peptides find a variety of therapeutic, diagnostic and related uses, e.g., to bind the receptor or an analogue thereof and inhibit or promote its activity.

In one embodiment the invention relates to methods for identifying the peptides which bind to the preselected receptor molecule. In certain aspects the methods generally comprise constructing a bacteriophage expression vector which comprises an oligonucleotide library of at least about $10^6$ members which encode the peptides. The library member is joined in reading frame to the 5' region of a nucleotide sequence encoding an outer structural protein of the bacteriophage. Appropriate host cells are transformed with the expression vectors, generally by electroporation, and the transformed cells cultivated under conditions suitable for expression and assembly of bacteriophage particles. Using a affinity screeing process, bacteriophage particles whose coat proteins have peptides which bind the receptor molecule are identified. The nucleotide sequence which encodes the peptide on the selected phage may then be determined. By repeating the affinity selection process one or more times, the peptides of interest may be enriched. By increasing the stringency of the selection, peptides of increasingly higher affinity may be identified.

In another aspect the methods are concerned with expression vectors having the oligonucleotide library members joined in reading frame with a nucleotide sequence to encode a fusion protein, wherein the library member represents the 5' member of the fusion and the 3' member comprises at least a portion of an outer structural protein of the bacteriophage. The first residue of the peptide encoded by the library member may be at the 5'-terminus of the sequence encoding the phage coat protein. In preferred embodiments, where phage proteins are initially expressed as preproteins and then processed by the host cell to a mature protein, the library members are inserted so as to leave the peptide encoded thereby at the N-terminus of the mature phage protein after processing or a protein substantially homologous thereto.

The invention also concerns host cells transformed with a bacteriophage expression vector having an oligonucleotide library member, joined in reading frame to the 5' region of a nucleotide sequence encoding an outer structural protein of the bacteriophage, wherein the library member encodes a peptide of at least about five to twenty-five amino acids.

Generally, the oligonucleotide library of the invention comprises a variable codon region which encodes for the peptides of interest, and may optionally comprise sequences coding for one or more spacer amino acid residues, such as Gly. The variable region may be encoded by $(NNK)_x$ or $(NNS)_x$, where N is A, C, G or T, K is G or T, S is G or C, and x is from 5 to at least about 8. In certain preferred embodiments the variable region of the oligonucleotide library member encodes a hexa-peptide. The variable codon region may also be prepared from a condensation of activated trinucleotides.

BRIEF DESCRIPTION OF THE DRAWINGS

FIG. 1(A) The vector fAFF1 contains two non-complementary BstXI sites separated by a 30 bp stuffer fragment (disclosed as SEQ ID NOS 1 and 3, encoding SEQ ID NO: 2). Removal of BstXI fragment (remaining vector fragments disclosed as SEQ ID NOS 4-7, respectively in order of appearance) allows oriented ligation of oligonucleotides with the appropriate cohesive ends (SEQ ID NO: 131 encoding SEQ ID NOS 9 and 12). Base pairs 1-30 and 49-85 of SEQ ID NO: 131 are disclosed as SEQ ID NOS 8 and 11. Their complements are disclosed as SEQ ID NOS 10 and 13. FIG. 1(B) The oligonucleotide ON-49 was annealed to two "half-site" fragments (SEQ ID NOS 15 and 17) to form cohesive termini complementary to BstXI sites 1 and 2 in the vector. The gapped structure, where the single-stranded region comprises the variable hexacodon sequence and a 2 (gly) codon spacer was ligated to the vector and electro-transformed into E. coli (SEQ ID NO: 130). Base pairs 1-10 and 29-49 of SEQ ID NO: 130 are disclosed as SEQ ID NOS 14 and 16.

FIG. 2 depicts the amino acid sequences (deduced from DNA sequence) of the N-terminal hexapeptides on pIII of infectious phage randomly chosen from the library. Sequences begin at the signal peptidase site. Single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), Y (Tyr) (SEQ ID NOS:18-69).

FIG. 4 shows the amino acid sequences (deduced from DNA sequence) of the N-terminal peptides of pIII of 52 phage isolated by three rounds of panning on mAB 3E7 (SEQ ID NOS:70-78, 78-91, and 91-119, respectively in order of appearance).

DESCRIPTION OF THE PREFERRED EMBODIMENTS

Figure 1:
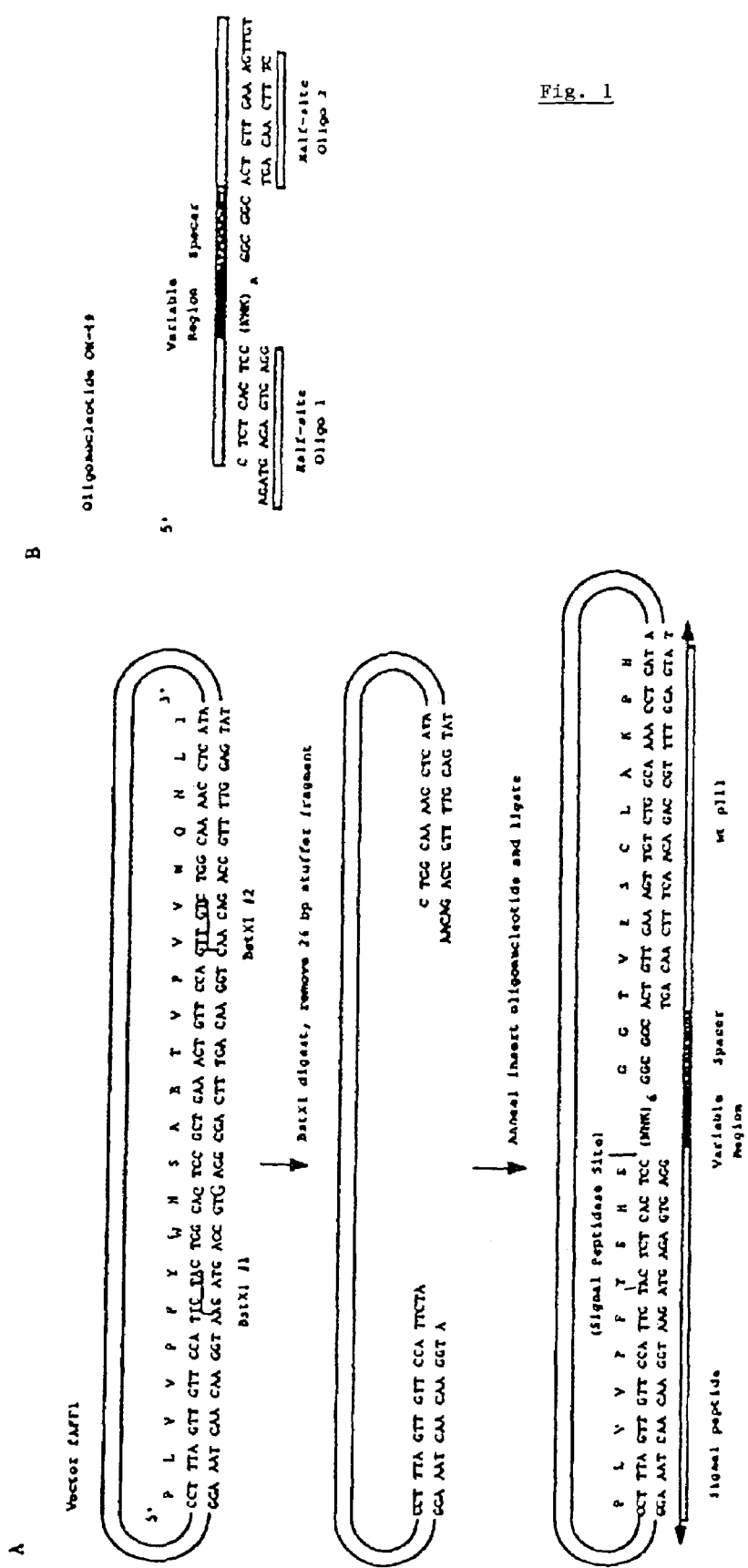
FIG. 1 depict the construction of an oligonucleotide library.

Methods and compositions are provided for identifying peptides which bind to receptor molecules of interest. The peptides are produced from oligonucleotide libraries which encode peptides attached to a bacteriophage structural protein. A method of affinity enrichment allows a very large library of peptides to be screened and the phage carrying the desired peptide(s) selected. The nucleic acid may then be isolated from the phage and the variable region of the oligonucleotide library member sequenced, such that the amino acid sequence of the desired peptide is deduced therefrom. Using these methods a peptide identified as having a binding affinity for the desired molecule may then be synthesized in bulk by conventional means.

By identifying the peptide de novo one need not know the sequence or structure of the receptor molecule or the sequence of its natural binding partner. Indeed, for many "receptor" molecules a binding partner has not yet been identified. A significant advantage of the present invention is that no prior information regarding an expected ligand structure is required to isolate peptide ligands of interest.

The number of possible receptor molecules for which peptide ligands may be identified by means of the present invention is virtually unlimited. For example, the receptor molecule may be an antibody (or a binding portion thereof). The antigen to which the antibody binds may be known and perhaps even sequenced, in which case the invention may be used to map epitopes of the antigen. If the antigen is unknown, such with certain autoimmune diseases, for example, peptides identified by these methods using, e.g., sera from patients with the disease as a receptor may be used to identify the antigen. Thus it may also be possible using these methods to tailor a peptide to fit a particular individual's disease. Once a peptide has been identified it may itself serve as, or provide the basis for, the development of a vaccine, a therapeutic agent, a diagnostic reagent, etc.

Other examples of receptor molecules for which the present invention may serve to identify peptide ligands include, by way of example and not limitation, growth factors, hormones, enzymes, interferons, interleukins, intracellular and intercellular messengers, cellular adhesion molecules and the like, and the corresponding receptors for the aforementioned molecules. It will be recognized that peptide ligands may also be identified by the present invention for molecules which are not proteins, e.g., carbohydrates, non-protein organic compounds, etc.

An oligonucleotide library, prepared according to the criteria as described herein, is inserted in an appropriate vector encoding a bacteriophage structural protein, preferably an accessible phage protein, such as a bacteriophage coat protein. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. In a more preferred embodiment the filamentous phage is fd, and contains a selectable marker such as tetracycline (e.g., "fd-tet"). The fd-tet vector has been extensively described in the literature. See, for example, Zacher et al., *Gene* 9:127-140 (1980), Smith et al., *Science* 228:1315-1317 (1985) and Parmley and Smith, *Gene* 73:305-318 (1988), each incorporated by reference herein.

The phage vector is chosen to contain or is constructed to contain a cloning site located in the 5' region of the gene encoding the bacteriophage structural protein, so that the peptide is accessible to receptors in an affinity enrichment procedure as described below. The structural phage protein is preferably a coat protein; in phage fd, an appropriate and preferred coat protein is pIII. Each filamentous fd phage is known to have up to four or five copies of the pIII protein.

An appropriate vector allows oriented cloning of the oligonucleotide sequences which encode the peptide so that the peptide is expressed at or within a distance of about 100 amino acid residues of the N-terminus of the mature coat protein. The coat protein is typically expressed as a preprotein, having a leader sequence. Thus, desirably the oligonucleotide library is inserted so that the N-terminus of the processed bacteriophage outer protein is the first residue of the peptide, i.e., between the 3'-terminus of the sequence encoding the leader protein and the 5'-terminus of the sequence encoding the mature protein or a portion of the 5' terminus.

The library is constructed by cloning an oligonucleotide which contains the variable region of library members (and any spacers, as discussed below) into the selected cloning site. Using known recombinant DNA techniques (see generally, Sambrook et al., *Molecular Cloning, A Laboratory Manual,* 2d ed., Cold Spring Harbor Laboratory Press, Cold Spring Harbor, N.Y., 1989, incorporated by reference herein), an oligonucleotide may be constructed which, inter alia, removes unwanted restriction sites and adds desired ones, reconstructs the correct portions of any sequences which have been removed (such as a correct signal peptidase site, for example), inserts the spacer residues, if any, and corrects the translation frame (if necessary) to produce active, infective phage. The central portion of the oligonucleotide will generally contain one or more of the variable region domain(s) and the spacer residues. The sequences are ultimately expressed as peptides (with or without spacer residues) fused to or in the N-terminus of the mature coat protein on the outer, accessible surface of the assembled bacteriophage particles.

The variable region domain of the oligonucleotide comprises the source of the library. The size of the library will vary according to the number of variable codons, and hence the size of the peptides, which are desired. Generally the library will be at least about $10^6$ members, usually at least $10^7$, and typically $10^8$ or more members. To generate the collection of oligonucleotides which forms a series of codons encoding a random collection of amino acids and which is ultimately cloned into the vector, a codon motif is used, such as $(NNK)_x$, where N may be A, C, G, or T (nominally equimolar), K is G or T (nominally equimolar), and x is typically up to about 5, 6, 7, or 8 or more, thereby producing libraries of penta-, hexa-, hepta-, and octa-peptides or more. The third position may also be G or C, designated "S". Thus, NNK or NNS (i) code for all the amino acids, (ii) code for only one stop codon, and (iii) reduce the range of codon bias from 6:1 to 3:1. It should be understood that with longer peptides the size of the library which is generated may become a constraint in the cloning process. The expression of peptides from randomly generated mixtures of oligonucleotides in appropriate recombinant vectors is discussed in Oliphant et al., *Gene* 44:177-183, incorporated herein by reference.

The exemplified codon motif $(NNK)_6$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with only three-codon amino acids.

An alternative approach to minimize the bias against one-codon residues involves the synthesis of 20 activated trinucleotides, each representing the codon for one of the 20 genetically encoded amino acids. These are synthesized by conventional means, removed from the support but maintaining the base and 5-HO-protecting groups, and activating by the addition of 3'O-phosphoramidite (and phosphate protection with b-cyanoethyl groups) by the method used for the activation of mononucleosides, as generally described in McBride and Caruthers, *Tetrahedron Letters* 22:245 (1983), which is incorporated by reference herein. Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis*, M. J. Gait, ed. p35-82 (1984). Thus, this procedure generates a population of oligonucleotides for cloning that is capable of encoding an equal distribution (or a controlled unequal distribution) of the possible peptide sequences. This approach may be especially employed in generating longer peptide sequences, since the range of bias produced by the $(NNK)_6$ motif increases by three-fold with each additional amino acid residue.

When the codon motif is $(NNK)_x$, as defined above, and when x equals 8, there are $2.6 \times 10^{10}$ possible octa-peptides. A library containing most of the octa-peptides may be difficult to produce. Thus, a sampling of the octa-peptides may be accomplished by constructing a subset library using up to about 10% of the possible sequences, which subset of recombinant bacteriophage particles is then screened. If desired, to extend the diversity of a subset library, the recovered phage subset may be subjected to mutagenesis and then subjected to subsequent rounds of screening. This mutagenesis step may be accomplished in two general ways: the variable region of the recovered phage may be mutagenized, or additional variable amino acids may be added to the regions adjoining the initial variable sequences.

To diversify around peptides found in early rounds of panning to have some binding activity, the positive phage are sequenced to determine the identity of the active peptides. Oligonucleotides are then synthesized based on these peptide sequences. The syntheses are done with a low level of all bases incorporated at each step to produce slight variations of the primary oligonucleotide sequences. This mixture of (slightly) degenerate oligonucleotides is then cloned into the affinity phage as described herein. This method produces systematic, controlled variations of the starting peptide sequences. It requires, however, that individual positive phage be sequenced before mutagenesis, and thus is useful for expanding the diversity of small numbers of recovered phage.

An alternate approach to diversify the selected phage allows the mutagenesis of a pool, or subset, of recovered phage. Phage recovered from panning are pooled and single stranded DNA is isolated. The DNA is mutagenized by treatment with, e.g., nitrous acid, formic acid, or hydrazine. These treatments produce a variety of damage in the DNA. The damaged DNA is then copied with reverse transcriptase which misincorporates bases when it encounters a site of damage. The segment containing the sequence encoding the variable peptide is then isolated by cutting with restriction nuclease(s) specific for sites flanking the variable region. This mutagenized segment is then recloned into undamaged vector DNA in a manner similar to that described herein. The DNA is transformed into cells and a secondary library is constructed as described. The general mutagenesis method is described in detail in Myers, et al., *Nucl. Acids Res.* 13:3131-3145 (1985), Myers et al., *Science* 229:242-246 (1985), and Myers, *Current Protocols in Molecular Biology* Vol I, 8.3.1-8.3.6, F. Ausebel, et al., eds, J. Wiley and Sons, New York (1989), each of which are incorporated herein by reference.

In the second general approach, that of adding additional amino acids to a peptide or peptides found to be active, a variety of methods are available. In one, the sequences of peptides selected in early panning are determined individually and new oligonucleotides, incorporating the determined sequence and an adjoining degenerate sequence, are synthesized. These are then cloned to produce a secondary library.

In another approach which adds a second variable region to a pool of peptide-bearing phage, a restriction site is installed next to the primary variable region. Preferably, the enzyme should cut outside of its recognition sequence, such as BspMI which cuts leaving a four base 5' overhang, four bases to the 3' side of the recognition site. Thus, the recognition site may be placed four bases from the primary degenerate region. To insert a second variable region, the pool of phage DNA is digested and blunt-ended by filling in the overhang with Klenow fragment. Double-stranded, blunt-ended, degenerately synthesized oligonucleotide is then ligated into this site to produce a second variable region juxtaposed to the primary variable region. This secondary library is then amplified and screened as before.

While in some instances it may be appropriate to synthesize longer peptides to bind certain receptors, in other cases it may be desirable to provide peptides having two or more regions of diversity separated by spacer residues. For example, the variable regions may be separated by spacers which allow the diversity domains of the peptides to be presented to the receptor in different ways. The distance between variable regions may be as little as one residue, sometimes five to ten and on up to about 100 residues. Or, for probing a large binding site the diverse regions may be separated by a spacer of residues of 20 to 30 amino acids. The number of spacer residues when present will preferably be at least two, typically at least three or more, and often will be less than ten, more often less than eight residues.

The oligonucleotide library may have variable domains which are separated by spacers, and thus may be represented by the formula:

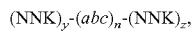

$(NNK)_y\text{-}(abc)_n\text{-}(NNK)_z,$ where N and K are as defined previously (note that S as defined previously may be substituted for K), and y+z is equal to about 5, 6, 7, 8, or more, a, b and c represent the same or different nucleotides comprising a codon encoding spacer amino acids, n is up to about 20 to 30 amino acids or more.

The spacer residues may be somewhat flexible, comprising oligo-glycine, for example, to provide the diversity domains of the library with the ability to interact with sites in a large binding site relatively unconstrained by attachment to the phage protein. Rigid spacers, such as, e.g., oligo-proline, may also be inserted separately or in combination with other spacers, including Gly. It may be desired to have the variable domains close to one another and use a spacer to orient the variable domain with respect to each other, such as by employing a turn between the two sequences, as might be provided by a spacer of the sequence Gly-Pro-Gly, for example. To add stability to such a turn, it may be desirable or necessary to add Cys residues at either or both ends of each variable region. The Cys residues would then form disulfide bridges to hold the variable regions together in a loop, and in this fashion may also serve to mimic a cyclic peptide. Of course, those skilled in the arts will appreciate that various other types of covalent linkages for cyclization may also be accomplished.

Spacer residues as described above may also be situated on either or both ends of the variable nucleotide region. For instance, a cyclic peptide may be accomplished without an intervening spacer, by having a Cys residue on both ends of the peptide. As above, flexible spacers, e.g., oligo-glycine, may facilitate interaction of the peptide with the selected receptors. Alternatively, rigid spacers may allow the peptide to be presented as if on the end of a rigid arm, where the number of residues, e.g., Pro, determines not only the length of the arm but also the direction for the arm in which the peptide is oriented. Hydrophilic spacers, made up of charged and/or uncharged hydrophilic amino acids, (e.g., Thr, His, Asn, Gln, Arg, Glu, Asp, Met, Lys, etc.), or hydrophobic spacers of hydrophobic amino acids (e.g., Phe, Leu, Ile, Gly, Val, Ala, etc.) may be used to present the peptides to binding sites with a variety of local environments.

Some peptides, because of their size and/or sequence, may cause severe defects in the infectivity of their carrier phage. This causes a loss of phage from the population during reinfection and amplification following each cycle of panning. To minimize problems associated with defective infectivity, DNA prepared from the eluted phage is transformed into appropriate host cells, such as, e.g., *E. coli*, preferably by electroporation, as described in, for example, Dower et al., *Nucl. Acids Res.* 16:6127-6145, incorporated herein by reference, or well known chemical means. The cells are cultivated for a period of time sufficient for marker expression, and selection is applied as typically done for DNA transformation. The colonies are amplified, and phage harvested as described below for affinity enrichment as described below. Phage identified in the affinity enrichment may be re-amplified by infection into the host cells.

The successful transformants are selected by growth in an appropriate antibiotic(s) which, in the case of the fd-tet vector, is tetracycline. This may be done on solid or in liquid growth medium. For growth on solid medium, the cells are grown at a high density ($\sim 10^8$ to $10^9$ tfs per m$^2$) on a large surface of, for example, L-agar containing the selective antibiotic to form essentially a confluent lawn. The cells and extruded phage are scraped from the surface and phage are prepared for first round of panning essentially as described by Parmley and Smith, *Gene* 73:305-318 (1988). For growth in liquid culture, cells may be grown in L-broth and antibiotic through about 10 or more doublings. The phage are harvested by standard procedures (see Sambrook et al., *Molecular Cloning*, 2nd ed. (1989), supra, for preparation of M13 phage) as described below. Growth in liquid culture may be more convenient because of the size of the libraries, while growth on solid media likely provides less chance of bias during the amplification process.

For affinity enrichment of desired clones, generally about $10^3$ to $10^4$ library equivalents (a library equivalent is one of each recombinant; $10^4$ equivalents of a library of $10^9$ members is $10^9 \times 10^4 = 10^{13}$ phage), but typically at least 102 library equivalents but up to about $10^5$ to $10^6$ are incubated with a receptor (or portion thereof) to which the desired peptide is sought. The receptor is in one of several forms appropriate for affinity enrichment schemes. In one example the receptor is immobilized on a surface or particle, and the library of phage bearing peptide is then panned on the immobilized receptor generally according to the procedure described below.

A second example of receptor presentation is receptor attached to a recognizable ligand (which may be attached via a tether). A specific example of such a ligand is biotin. The receptor, so modified, is incubated with the library of phage and binding occurs with both reactants in solution. The resulting complexes are then bound to streptavidin (or avidin) through the biotin moiety. The streptavidin may be immobilized on a surface such as a plastic plate or on particles, in which case the complexes (phage/peptide/receptor/biotin/streptavidin) are physically retained; or the streptavidin may be labelled, with a fluorophore, for example, to tag the active phage/peptide for detection and/or isolation by sorting procedures, e.g., on a fluorescence-activated cell sorter.

The phage bearing peptides without the desired specificity are removed by washing. The degree and stringency of washing required will be determined for each receptor/peptide of interest. A certain degree of control can be exerted over the binding characteristics of the peptides recovered by adjusting the conditions of the binding incubation and the subsequent washing. The temperature, pH, ionic strength, divalent cation concentration, and the volume and duration of the washing will select for peptides within particular ranges of affinity for the receptor. Selection based on slow dissociation rate, which is usually predictive of high affinity, is the most practical route. This may be done either by continued incubation in the presence of a saturating amount of free ligand, or by increasing the volume, number, and length of the washes. In each case, the rebinding of dissociated peptide-phage is prevented, and with increasing time, peptide-phage of higher and higher affinity are recovered. Additional modifications of the binding and washing procedures may be applied to find peptides which bind receptors under special conditions.

Although the phage panning method is highly specific, the procedure generally does not discriminate between peptides of modest affinity (micromolar dissociation constants) and those of high affinity (nanomolar dissociation constants or greater). The ability to select phage bearing peptides with relatively low affinity may be result of multivalent interaction between a phage/peptide particle and a receptor. For instance, when the receptor is an IgG antibody, each phage bearing peptides may bind to more than one antibody binding site, either by a single phage binding to both sites of single IgG molecule or by forming network of phage-IgG which multivalent interaction produces a high avidity and tenacious adherence of the phage during washing. To enrich for the highest affinity peptide ligands, a monovalent interaction between phage and the immobilized receptor may thus be appropriate.

A strategy employing a combination of conditions favoring multivalent or monovalent interactions may be used to advantage in discovering new peptide ligands for receptor proteins. By conducting the first rounds of panning under conditions to promote multivalent interactions, high stringency washing can be used to greatly reduce the background of non-specifically bound phage. This high avidity step may select a large pool or peptides with a wide range of affinities, including those with relatively low affinity. It may select for specific recognition kernels, such as the Tyr-Gly dipeptide described in the examples below. Subsequent panning under conditions favoring monovalent interactions and isolation of phage based on a slow dissociation rate may then allow the identification of the highest affinity peptides. Monovalent interactions may be achieved by employing low concentrations of receptor (for example, $10^{-1}$ to $10^{-3} \times Kd$ or even less).

Once a peptide sequence that imparts some affinity and specificity for the receptor molecule is known, the diversity around this "recognition kernel" may be embellished. For instance, variable peptide regions may be placed on one or both ends of the identified sequence. The known sequence may be identified from the literature, as in the case of Arg-Gly-Asp and the integrin family of receptors, for example, as described in Ruoslahti and Pierschbacher, *Science* 238:491-497 (1987), or may be derived from early rounds of panning in the context of the present invention.

Libraries of peptides on phage produced and screened according to the present invention are useful for, e.g., mapping antibody epitopes. The ability to sample a large number of potential epitopes as described herein has clear advantages over the methods based on chemical synthesis now in use and described in, among others, Geysen et al., *J. Immunol. Meth.* 102:259-274 (1987). In addition, these libraries are useful in providing new ligands for important binding proteins such as hormone receptors, enzymes, etc.

Accordingly, the following examples are offered by way of illustration, not by way of limitation.

EXAMPLE I

Reagents and Strains

BstXI restriction endonuclease, T4 DNA ligase, and T4 kinase were obtained from New England Biolabs. Streptavidin and biotinylated goat anti-mouse IgG were obtained from BRL. Sequenase 2.0 was obtained from U.S. Biochemical. Monoclonal antibody 3E7 used in initial studies was provided by A. Herz and is described in Meo et al., infra., incorporated herein by reference, and was also purchased from Gramsch Laboratories (Schwabhausen, West Germany). [$^{125}$I-tyr$^{28}$]b-endorphin (2000 Ci/mmol) was purchased from Amersham Corp. (Arlington Heights, Ill.). Oligonucleotides were synthesized with an Applied BioSystems PCR-Mate and purified on OPC columns (ABI). Peptides were synthesized with an Applied BioSystems 431A (Foster City, Calif.) or Biosearch model 9600 (San Rafael, Calif.) synthesizer and purified to greater than 95% purity by reverse phase HPLC. Peptide content of the pure peptides was determined by amino acid analysis and the composition was verified by FAB-MS. Bacteriophage fd-tet and *E. coli* K91 were provided by G. Smith, Univ. of Missouri, Columbia, Mo. 65211, and are described in, among others, Zacher et al., *Gene* 9:127-140 (1980), Smith et al., *Science* 228:1315-1317 (1985) and Parmley and Smith, *Gene* 73:305-318 (1988).

Construction of Vector fAFF1

A filamentous bacteriophage vector was constructed from the tetracycline resistance transducing vector fdTet, described in Zacher et al., supra. The vector, designated fAFF1, was designed to provide many choices in the size and location of the peptides expressed fused to the pIII bacteriophage coat protein. pIII is made as a preprotein with an 18 amino acid leader sequence that directs pIII to the inner membrane of the bacterial host cell before it becomes assembled into an intact phage particle (Goldsmith and Konigsberg, *Biochem.* 16:2686-2694 (1977) and Boeke and Model, *Proc. Natl. Acad. Sci. USA* 79:5200-5204 (1982) incorporated herein by reference). As explained further below, a peptide library was constructed by cloning an oligonucleotide of the structure shown in FIG. 1B to place the variable hexapeptide region at the N-terminus of the processed protein. These first six residues are followed by two glycines and then the normal sequence of pIII. The library consists of about $3 \times 10^8$ independent recombinants.

A cloning site, consisting of two non-complementary BstXI sites, was engineered into the 5'-region of gene III. As shown in FIG. 1A, two non-complementary BstXI sites flank the region encoding amino acids surrounding the signal peptidase site (the N-terminus of the mature pIII). fAFF1 also has a −1 frameshift mutation in pIII that results in non-infective phage. By removing the BstXI fragment and inserting an oligonucleotide of the appropriate structure, (a) portions of the removed sequence can be precisely reconstructed (the correct signal peptide site, for example,) (b) one or more additional amino acids may be expressed at several locations, and (c) the correct translation frame is restored to produce active, infective pIII.

Construction of the cloning site at the 5'-region of gene III was accomplished by first removing a BstXI restriction site already present in the TN10 region of fdTet, RF DNA was digested with BstXI restriction endonuclease, and T4 DNA polymerase was added to remove the protruding 3' termini. Blunt-ended molecules were then ligated and transformed into MC1061 cells. RF DNA isolated from several tetracycline resistant transformants was digested again with BstXI; a clone that was not cleaved was selected for construction of the double BstXI site. Site-directed mutagenesis (Kunkel et al., *Meth. Enzymol.* 154:367-382 (1987), incorporated by reference herein) was carried out with the oligonucleotide 5'-TAT GAG GTT TTG CCA GAC AAC TGG AAC AGT TTC AGC GGA GTG CCA GTA GAA TGG AAC AAC TAA AGG (SEQ ID NO:120). Insertion of the correct mutagenic sequence was confirmed by dideoxy sequencing of RF DNA isolated from several tetracycline-resistant transformants.

Construction of a Diverse Oligonucleotide Library

Oligonucleotides which were cloned have the general structure shown in FIG. 1B. The 5' and 3' ends have a fixed sequence, chosen to reconstruct the amino acid sequence in the vicinity of the signal peptidase site. The central portion contained the variable regions which comprise the oligonucleotide library members, and may also code for spacer residues on either or both sides of the variable sequence.

A collection of oligonucleotides encoding all possible hexapeptides was synthesized with the sequence 5'-C TCT CAC TCC(NNK)$_6$ GGC GGC ACT GTT GAAAGT TGT-3' (SEQ ID NO:130). N was A, C, G, and T (nominally equimolar), and K was C and T (nominally equimolar). This sequence, designated ON49, was ligated into the BstXI sites of fAFF1 after annealing to two "half-site" oligonucleotides, ON-28 (5'-GGA GTG AGA GTA GA-3') (SEQ ID NO:121) and ON-29 (5'-CTT TCA ACA GT-3') (SEQ ID NO:122), which are complementary to the 5'- and 3'-portions of ON-49, respectively. "Half-site" oligonucleotides anneal to the 5'- and 3'-ends of oligonucleotide ON-49 to form appropriate BstXI cohesive ends.

This left the appropriate BstXI site exposed without the need to digest with BstXI, thus avoiding the cutting of any BstXI sites that might have appeared in the variable region. The vector fAFF1 (100 µg) was digested to completion with BstXI, heat inactivated at 65.degree. C., and ethanol precipitated twice in the presence of 2M ammonium acetate. Oligonucleotides were phosphorylated with T4 kinase, and annealed in 20 mM Tris-HCl, pH 7.5, 2 mM MgCl.sub.2, 50 mM NaCl, by mixing 1.5 µg ON-28, 1.2 µg ON-29, and 0.5 µg ON-49 with 20 µg BstXI-digested fAFF1 RF DNA, heating to 65° C. for 5 minutes and allowing the mixture to cool slowly to room temperature. This represented an approximate molar ratio of 1:5:100:100 (fAFF1 vector: ON-49: ON-28: ON-29). The annealed structure is then ligated to BstXI-cut fAFF1 RF DNA to produce a double-stranded circular molecule with a small, single stranded gap. These molecules may be transformed into host cells. The annealed DNA was ligated in 20 mM Tris-HCl, pH 7.5, 5 mM MgCl$_2$, 2 mM DTT, 1 mM ATP, by the addition of 20 units of T4 DNA ligase and incubated overnight at 15° C.

Alternatively, before transformation, the gap may be filled-in under conditions disfavoring secondary structure in the variable region. In some experiments the gapped circular structure created by this ligation was filled in with T4 DNA polymerase in the presence of ligase and dNTPs (400 µM each) to produce a covalently closed, double-stranded molecule (Kunkel et al., supra). The ligated DNA was ethanol precipitated in the presence of 0.3 M sodium acetate, resuspended in water, and transformed by electroporation into MC1061. Five electro-transformations, each containing 80 µl of cells and 4 µg of DNA (50 µg/ml), were performed by pulsing at 12.5 kV/cm for 5 msec as described in Dower et al., Nucleic Acids Res. 16:6127-6145 (1988), incorporated by reference herein. After one hour of non-selective outgrowth at 37° C. in 2 ml of SOC medium (2% Bacto tryptone, 0.5% Bacto yeast extract, 10 mM NaCl, 2.5 mM KCl, 10 mM MgCl$_2$, 10 mM MgSO$_4$, 20 mM glucose; see Hanahan, J. Mol. Biol. 166:557-580 (1983)), the transformations were pooled, an aliquot was removed, and several dilutions were plated on LB agar plates containing tetracycline (20 µg/ml) to assess the transformation efficiency. The remainder was used to inoculate one liter of L-broth containing tetracycline (20 µg/ml) and was grown through approximately 10 doublings at 37° C. to amplify the library.

Isolation of Phage

Phage from liquid cultures were obtained by clearing the supernatant twice by centrifugation (8000 RPM for 10 min in JA10 rotor, at 4°), and precipitating phage particles with polyethylene glycol (final concentration 3.3% polyethylene glycol-8000, 0.4 M Naci), and centrifuged as described above. Phage pellets were resuspended in TBS (50 mM Tris-HCl, pH 7.5, 150 mM NaCl) and stored at 4° C. In some cases, phage were isolated from plate stocks by scraping from the agar surface, resuspending in L-broth, and purifying as described above.

Affinity Purification

Approximately $10^3$ to $10^4$ library equivalents of phage were reacted overnight with 1 µg of purified antibody in 1 ml TBS at 4° C. (Under these conditions, phage and antibody are about equimolar; therefore, antibody is in great excess over the phage ligand peptides.) Phage expressing peptides with affinity for mAb3E7 were isolated by a modification of the procedure of Parmley and Smith, supra. A 60×15 mm polystyrene petri plate was coated with 1 ml of streptavidin solution (1 mg/ml streptavidin in 0.1 M NaHCO$_3$, pH 8.6, 0.02% NaN$_3$) and incubated overnight at 4° C. The streptavidin solution was removed the following day. The plate was filled with 10 ml blocking solution (30 mg/ml BSA, 3 µg/ml streptavidin in 0.1 M NaHCO$_3$, pH 9.2, 0.02% NaN$_3$) and incubated for two hours at room temperature. Biotinylated goat anti-mouse IgG (2 µg) was added to the antibody-reacted phage library and incubated for two hours at 4° C. Immediately before panning, the blocking solution was removed from the streptavidin-coated plate, and the plate was washed 3 times with TBS/0.05% Tween 20. The antibody-reacted phage library was then added to the plate and incubated for 30 min. at room temperature. The phage solution was removed and the plate was washed ten times with 10 ml TBS/0.05% Tween 20 over a period of 60 min. at room temperature. Adherent phage were removed by adding 800 µl of elution buffer (1 mg/ml BSA in 0.1 N HCl adjusted to pH 2.2 with glycine) to the petri plate and incubating for 10 min. to dissociate the immune complexes. The eluate was removed, neutralized by addition of 45 µl of 2 M Tris base, and used to infect log phase E. coli K91 cells.

The infected cells were then plated on LB agar plates containing tetracycline (20 µg/ml), and grown overnight at 37° C. Phage were isolated from these plates as described above and the affinity purification process was repeated for two more rounds. After each round of panning and amplification, DNA of phage from several thousand colonies was pooled and sequenced to estimate the diversity in the cloning site. In the first two positions of each codon, bands of about the same intensity appeared in each lane, indicating the expected distribution of bases in these positions. In the third position of each codon the G band was somewhat more intense than the T band.

After the final round of panning and amplification, a portion of the eluate was used to infect cells that were plated at low density on LB tetracycline plates. To analyze the diversity of peptide sequences in the library in a more direct way, we picked 52 individual colonies producing infectious phage, and sequenced the DNA of their variable regions. Individual colonies were picked and transferred to culture tubes containing 2 ml LB tetracycline and grown to saturation. Phage DNA was isolated by a method designed for the Beckman Biomek Workstation employing 96-well microtiter plates (Mardis and Roe, Biotechniques 7:840-850 (1989), incorporated by reference herein). Single stranded DNA was sequenced using Sequenase 2.0 and an oligonucleotide sequencing primer (5'-CGA TCT AAA GTT TTG TCG TCT-3') (SEQ ID NO:123) which is complementary to the sequence located 40 nucleotides to the 3' side of the second BstXI site in fAFF1.

The distribution of bases at each position within each codon is given in Table 1. The first two positions of each codon have close to the expected equimolar distribution of the four bases. The third position is significantly biased, containing about 50% more G than T in this sample. This bias is most likely introduced during the chemical synthesis of the oligonucleotide mixture, but may also reflect biological biases imposed on the expressed peptides.

TABLE 1

Nucleotide Distribution in the Diversity Region of Infectious Phage Randomly Selected from the Library.

| | Frequency of each base by position in codon (%) | | |
|---|---|---|---|
| | N | N | K |
| G | 31 | 27 | 59 |
| A | 22 | 22 | <1 |
| T | 25 | 26 | 39 |
| C | 22 | 24 | 1 |

In FIG. 2, the amino acid sequences are listed for the peptides encoded by the oligonucleotide inserts of a sample of randomly selected, infectious phage. The amino acid content of the expressed peptides from the 52 randomly selected infectious phage appears in Table 2.

TABLE 2

Amino Acid Content in the Variable Peptide of 52 Randomly-Selected Infectious Phage

| Amino Acid | Nominal Frequency | Nominal Occurrence | Observed Occurrence | Obs/Nom |
|---|---|---|---|---|
| A | 0.065 | 19 | 27 | 1.42 |
| C | 0.032 | 9 | 8 | 0.89 |
| D | 0.032 | 9 | 10 | 1.11 |
| E | 0.032 | 9 | 9 | 1.00 |
| F | 0.032 | 9 | 12 | 1.33 |
| G | 0.065 | 19 | 33 | 1.74 |
| H | 0.032 | 9 | 7 | 0.78 |
| I | 0.032 | 9 | 6 | 0.67 |
| K | 0.032 | 9 | 16 | 1.78 |
| L | 0.097 | 28 | 35 | 1.25 |
| M | 0.032 | 9 | 10 | 1.11 |
| N | 0.032 | 9 | 7 | 0.78 |
| P | 0.065 | 19 | 9 | 0.47 |
| Q | 0.032 | 9 | 15 | 1.67 |
| R | 0.097 | 28 | 29 | 1.04 |
| S | 0.097 | 28 | 30 | 1.07 |
| T | 0.065 | 19 | 14 | 0.74 |
| V | 0.065 | 19 | 18 | 0.95 |
| W | 0.032 | 9 | 11 | 1.22 |
| Y | 0.032 | 9 | 6 | 0.67 |

As shown in Table 2, the ratio of the observed occurrence of each amino acid to that expected on the basis of codon frequency ranges from about 0.5 to 2, consistent with a random distribution of sequences.

Constructing a library of peptides displayed on the N-terminus of processed pIII necessarily alters amino acids in the vicinity of the signal peptidase cleavage site. Certain changes in the corresponding region of the major coat protein, pVIII, have been shown to reduce processing efficiency, slowing or preventing the incorporation of pVIII to virions. If pIII were similarly affected, the diversity of peptides contained in the library would be reduced. The finding that most amino acids appear at each position of the variable peptides of randomly selected phage indicates that processing defects do not impose severe constraints on the diversity of the library.

Isolation and Sequencing of Phage having High Avidity for Anti-b-Endorphin Antibody.

Monoclonal antibody 3E7 binds to B-endorphin and, like the delta-opioid receptor, recognizes the N-terminal portion of the protein (Tyr-Gly-Gly-Phe) (SEQ ID NO:124), which is present on most natural opioid peptides. The antibody also binds tightly to leu- and met-enkephalin (YGGFL (SEQ ID NO:125), YGGFM (SEQ ID NO:126)), and a variety of related opioid peptides (Meo et al., Proc. Natl. Acad. Sci. USA 80:4084-4088 (1983), Herz et al., Life Sciences 31:1721-1724 (1982), and Gramsch et al., J. Neurochem. 40:1220-1226 (1983). The N-terminal hexapeptide library was screened against 3E7 by carrying out three rounds of panning, elution, and amplification. The recoveries of phage from this process are shown in Table 3. In each round the proportion of phage adsorbed to the antibody increased by about 100-fold, and in the last round, over 30% of the input phage were recovered. These results indicated that phage were preferentially enriched in each panning step.

TABLE 3

Recovery of Phage from Panning on mAb3E7

| Rounds of Panning | Input of Phage | Eluted Phage | Recovery Input/Eluted |
|---|---|---|---|
| 1 | $4.0 \times 10^{11}$ | $1.9 \times 10^7$ | $4.8 \times 10^{-5}$ |
| 2 | $2.0 \times 10^{11}$ | $5.0 \times 10^8$ | $2.5 \times 10^{-3}$ |
| 3 | $1.8 \times 10^{10}$ | $5.6 \times 10^9$ | $3.1 \times 10^{-1}$ |

Figure 3:
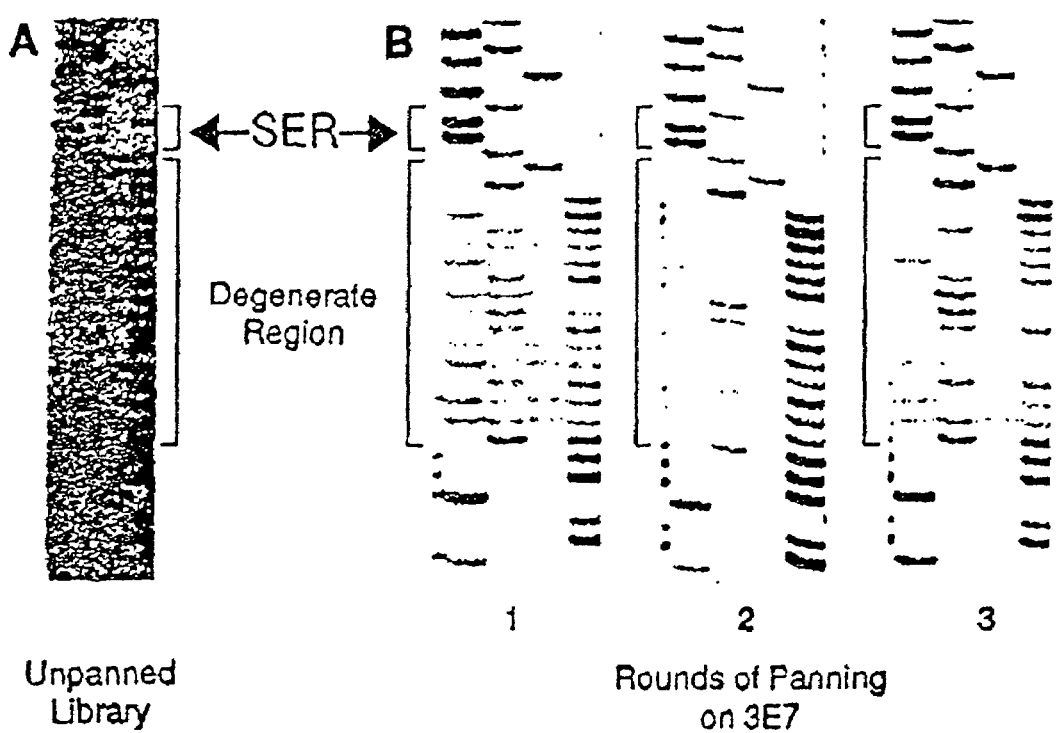
FIG. 3 illustrates the composite DNA sequence of the variable region of pools of (A) infectious phage from the library, and (B) phage recovered from 1, 2, or 3 rounds of panning on mAB 3E7. Phage were amplified as tetracycline resistant colonies and DNA from a pool of phage derived from several thousand of these colonies was isolated and sequenced. The area of the sequencing gel corresponding to the cloning site in geneIII is displayed. A sequencing primer was annealed to the phage DNA ~40 bases to the 3' side of the cloning site. The actual readout of the gel is the sequence complementary to the coding strand. For clarity of codon identification, the lanes may be read as C, T, A, G, left to right and 5' to 3', top to bottom, to identify the sequence of the coding (+) strand.

After each round of panning, DNA representing several thousand eluted phage was pooled and sequenced. The area of the sequencing gel corresponding to the insertion site in gene III is shown in FIG. 3. The codon TCC specifying the serine that precedes the variable region is indicated by an arrow. After the first round of panning, the codon following this serine was clearly enriched in TAT (the single codon for tyrosine). After the second round, virtually all first codons in the pooled DNA appeared to be TAT. The second codons are strongly GGK (the two codons for glycine). After three rounds of panning, it appeared that phage containing relatively few kinds of amino acids in the first four positions had been selected, whereas the fifth and sixth positions appeared to be as diverse as those in the starting phage population.

The DNA samples from 51 individual phage recovered from the third panning were sequenced. The deduced amino acid sequences of the N-terminal hexapeptides are shown in FIG. 4 and the amino acid distributions of these peptides are summarized in Table 4. Each of the 51 panned phages analyzed had an N-terminal tyrosine, and nearly all (94%) had a glycine in the second position. The third position in our sample is occupied by many amino acids, some of which are present more often than would be expected by chance. The fourth position is occupied primarily by the large aromatic residues Trp and Phe (together 50%), and the bulky hydrophobic residues Leu and Ile (an additional 45%). The fifth and sixth positions contain essentially random distributions of amino acids, with only alanine appearing at slightly greater than chance in position five.

TABLE 4

Distribution of Amino Acids in the Diversity Peptide of 51 Phage Selected by Panning With Anti-endorphin Antibody

| Residue Position | Amino Acid | Nominal | Observed Frequency | Enrichment[a] Frequency Ratio |
|---|---|---|---|---|
| 1 | Y | .031 | 1.00 | 33 |
| 2 | G | .062 | 0.94 | 16 |
|   | A, S |   |   | <1 |
| 3 | G | .062 | 0.31 | 5 |
|   | W | .031 | 0.10 | 3 |
|   | S | .093 | 0.21 | 2 |
|   | A | .062 | 0.12 | 2 |
|   | N | .031 | 0.06 | 2 |
|   | D, E, F, K, L, M, P, T, V |   |   | <1 |
| 4 | W | .031 | 0.31 | 10 |
|   | F | .031 | 0.19 | 6 |
|   | L | .093 | 0.35 | 4 |
|   | I | .031 | 0.10 | 3 |
|   | A, G, M |   |   | <1 |

[a] Observed frequency divided by nominal frequency.

EXAMPLE II

Binding Affinities of Peptides for Receptor Monoclonal Antibody 3E7

The affinity of peptides for the 3E7 antibody has been previously determined for those peptides related to naturally-occurring opioid peptides. Meo et al., supra. As none of the peptides identified by the procedure described herein had been previously described, six of these peptides were chemically synthesized and their binding affinities estimated.

The peptides were synthesized according to well known protocols, as described in, for example, Merrifield, *Science* 232:341-347 (1986), incorporated by reference herein. A solution radioimmunoassay was used to estimate the binding affinities of peptides for mAb 3E7. Solution radioimmunoassay using [$^{125}$I]b-endorphin (20,000 cpm) and purified 3E7 antibody (0.25 µg/ml) was conducted as described by Meo et al., supra, with the exception that the final volume was 150 µl. Antibody-bound and free [$^{125}$I]b-endorphin were separated by addition of activated charcoal followed by centrifugation, as described in Ghazarassian et al., *Life Sciences* 27:75-86 (1980). Antibody-bound [$^{125}$I]b-endorphin in the supernatant was measured in a gamma counter. For each peptide, inhibition of [$^{125}$I]b-endorphin was determined at six different concentrations at ⅓ log unit intervals and the 50% inhibitory concentration (IC50) was determined by fitting the data to a two-parameter logistic equation using the ALLFIT program, as described in DeLean et al., *Am. J. Physiol.* 235:E97-E102 (1978).

The previously reported high degree of specificity of the 3E7 antibody for the intact N-terminal epitope Tyr-Gly-Gly-Phe (SEQ ID NO:124) which is common to naturally occurring opioid peptides, Meo et al., supra, was verified. Removal of Tyr or deletion of any of the amino acids of the sequence Tyr-Gly-Gly-Phe-Leu (SEQ ID NO:125) had deleterious effect on binding affinity (Table 5).

Shown in Table 5 are the IC50 for the six peptides which were identified by the phage panning method and chemically synthesized. Under the conditions of the radioimmunoassay (30 pM [$^{125}$I]b-endorphin; 20% tracer bound; 18 hr. incubation), the IC50 should be very close to the dissociation constant (Kd) for the peptide. The peptides are all relatively low affinity compared to YGGFL (SEQ ID NO:125), with IC50's ranging from 0.35 to 8.3 µM.

TABLE 5

Relative affinities of peptides for 3E7 antibody determined by solution radioimmunoassay.[a]

| Peptide | SEQ ID NO | N | IC50 | (µM) | Affinity Relative to YGGFL (SEQ ID NO: 125) |
|---|---|---|---|---|---|
| YGGFL | SEQ ID NO: 125 | (6) | 0.0071 | (0.0054, 0.0093) | 1 |
| YGGF | SEQ ID NO: 124 | (3) | 0.19 | (0.093, 0.38) | 0.037 |
| YGGL | SEQ ID NO: 127 | (3) | 3.8 | (2.1, 6.6) | 0.0018 |
| YGFL | SEQ ID NO: 128 | (3) | 28 | (17, 47) | 0.00025 |
| YGG |  | (2) | >1000 |  | <0.0000071 |
| GGFL | SEQ ID NO: 129 | (2) | >1000 |  | <0.0000071 |
| GGF |  | (2) | >1000 |  | <0.0000071 |
| GFL |  | (2) | >1000 |  | <0.0000071 |
| YGFWGM | SEQ ID NO: 112 | (3) | 0.35 | (0.19, 0.63) | 0.020 |
| YGPFWS | SEQ ID NO: 114 | (3) | 1.9 | (1.3, 2.8) | 0.0037 |
| YGGFPD | SEQ ID NO: 83 | (3) | 2.3 | (1.4, 3.7) | 0.0031 |
| YGGWAG | SEQ ID NO: 79 | (3) | 7.8 | (6.0, 10) | 0.00091 |
| YGNWTY | SEQ ID NO: 104 | (3) | 7.8 | (4.0, 15) | 0.00091 |
| YAGFAQ | SEQ ID NO: 118 | (3) | 8.3 | (3.8, 18) | 0.00086 |

[a] = Data are geometric means and 95% confidence intervals (calculated from S.E.M. of log IC50) from the number (N) of independent determinations indicated.

The data indicate that although the phage panning method is highly specific in that no unrelated peptides were selected, the procedure apparently does not discriminate between those of moderate (µM Kd) and high (nM Kd) affinity. The six peptides chosen from among the 51 clones that were sequenced were only a small subset of those which were selected by three rounds of panning. Based on their structural diversity, the phage library should contain thousands of different peptides with dissociation constants that are µM or lower.

The panning procedure we have utilized employs extensive washing to remove non-specifically bound phage. Binding experiments with mAb 3E7 and [$^3$H]YGGFL (SEQ ID NO:125) indicate a rapid dissociation rate, approximately $t_{1/2}$=45 seconds at room temperature. Therefore, the ability to select phage bearing peptides with relatively low affinities may be the result of multivalent interaction between phage and antibody, as each phage typically has up to 4 or 5 copies of the pIII protein and each protein may carry a foreign peptide from the phage library.

Although the foregoing invention has been described in some detail by way of illustration and example for purposes of clarity of understanding, it will be apparent that certain changes and modifications may be practiced within the scope of the appended claims.

What is claimed is:

1. A method for identifying a polynucleotide sequence that encodes a peptide which binds to a preselected receptor molecule, comprising:
    (1) transforming host cells by electroporation with at least $10^8$ different filamentous bacteriophage expression vectors, wherein each of said different vectors comprises a polynucleotide sequence that encodes a fusion protein comprising a peptide fused to a pill coat protein of a filamentous bacteriophage so that the N-terminal amino acid of said fusion protein is the N-terminal amino acid of said peptide, and wherein said different vectors are constructed by ligating each polynucleotide of a mixture of at least $10^8$ different polynucleotides to a bacteriophage cloning vector that encodes the coat protein so as to form a coding sequence for said fusion protein, wherein each of said different polynucleotides comprises a series of codons encoding a random collection of amino acids and encodes a different peptide;
    (2) cultivating the transformed cell under conditions suitable for expression and assembly of bacteriophage particles thereby displaying said peptides on the surface of said particles;
    (3) selecting bacteriophage particles displaying the peptide by combining said particles with the preselected receptor molecule and separating particles bound to said receptor molecule from unbound particles; and
    (4) sequencing said polynucleotide sequence encoding said peptide within said selected bacteriophage particles.

2. A method for identifying a polynucleotide sequence that encodes a peptide which binds to a preselected receptor molecule, comprising:
    (1) transforming host cells by electroporation with at least $10^8$ different filamentous bacteriophage expression vectors, wherein each of said different vectors comprises a polynucleotide sequence that encodes a fusion protein comprising a peptide fused to a pill coat protein of a filamentous bacteriophage so that the N-terminal amino acid of said fusion protein is the N-terminal amino acid of said peptide, and wherein said different vectors differ from each other with respect to the peptide of said fusion protein encoded by said vector;
    (2) cultivating the transformed cell under conditions suitable for expression and assembly of bacteriophage particles thereby displaying said peptides on the surface of said particles;
    (3) selecting bacteriophage particles displaying the peptide by combining said particles with the preselected receptor molecule and separating particles bound to said receptor molecule from unbound particles; and
    (4) sequencing said polynucleotide sequence encoding said peptide within said selected bacteriophage particles,
    wherein each of said $10^8$ different polynucleotides is comprised of first, second, and third single-stranded oligonucleotides that are annealed to one another prior to insertion into said cloning vector; and
    wherein said first single stranded oligonucleotide is 5'C T C T C A C T C C (NNK)$_6$G G C G G C A C T G T T G A A A G T T G T(SEQ ID NO: 130); and said second and third single stranded oligonucleotides are 5'G G A G T G A G A G T A G A (SEQ ID NO: 121) and 5'C T T T C A A C A G T (SEQ ID NO: 122), respectively.

3. A method for identifying a polynucleotide sequence that encodes a peptide which binds to a preselected receptor molecule, comprising:
    (1) transforming host cells by electroporation with at least $10^8$ different filamentous bacteriophage expression vectors, wherein each of said different vectors comprises a polynucleotide sequence that encodes a fusion protein comprising a peptide fused to a pill coat protein of a filamentous bacteriophage so that the N-terminal amino acid of said fusion protein is the N-terminal amino acid of said peptide, and wherein said different vectors differ from each other with respect to the peptide of said fusion protein encoded by said vector;
    (2) cultivating the transformed cell under conditions suitable for expression and assembly of bacteriophage particles thereby displaying said peptides on the surface of said particles;
    (3) selecting bacteriophage particles displaying the peptide by combining said particles with the preselected receptor molecule and separating particles bound to immobilized preselected receptor molecule from unbound particles;
    (4) repeating the selection step at least once, wherein the selected bacteriophage particles are propagated between said selection step(s) and wherein said receptor is immobilized at reduced densities in subsequence repetitions of the selecting step; and
    (5) sequencing said polynucleotide sequence encoding said peptide within said selected bacteriophage particles.

* * * * *

SEQUENCE LISTING

<160> NUMBER OF SEQ ID NOS: 131

<210> SEQ ID NO 1
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(66)

<400> SEQUENCE: 1

```
cct tta gtt gtt cca ttc tac tgg cac tcc gct gaa act gtt cca gtt        48
Pro Leu Val Val Pro Phe Tyr Trp His Ser Ala Glu Thr Val Pro Val
1               5                   10                  15 gtc tgg caa aac ctc ata                                                66
Val Trp Gln Asn Leu Ile
            20
```

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

```
Pro Leu Val Val Pro Phe Tyr Trp His Ser Ala Glu Thr Val Pro Val
1               5                   10                  15

Val Trp Gln Asn Leu Ile
            20
```

<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
tatgaggttt tgccagacaa ctggaacagt ttcagcggag tgccagtaga atggaacaac        60
taaagg                                                                   66
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
cctttagttg ttccattcta                                                    20
```

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atggaacaac taaagg                                                    16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctggcaaaac ctcata                                                    16

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tatgaggttt tgccagacaa                                                20

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctttagttg ttccattcta ctctcactcc                                     30

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Leu Val Val Pro Phe Tyr Ser His Ser
1               5                   10

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggagtgagag tagaatggaa caactaaagg                                     30

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
ggcggcactg ttgaaagttg tctggcaaaa cctcata                                    37

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Thr Val Glu Ser Cys Leu Ala Lys Pro His
1               5                   10

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tatgaggttt tgccagacaa ctttcaacag t                                          31

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctctcactcc                                                                  10

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ggagtgagag taga                                                             14

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggcggcactg ttgaaagttg t                                                     21

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 17
ctttcaacag t                                                          11

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Met Leu Gln Arg Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Ser Arg Lys Leu Phe
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Trp Ala Gly His Glu
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Gly Ile Thr Gln Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Thr Ser Tyr Gly Gly
1               5

<210> SEQ ID NO 23
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 23

Gln Lys Arg Gly Glu Asp
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Leu Thr Lys Arg Gln
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Val Ser Leu Gln Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gly Ser Phe Glu Ala
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ile Ala Ala Arg Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Ala Arg Leu Gly Leu
1               5
```

-continued

```
<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Ala Phe Leu Ala Met
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Leu Ser Pro Lys Val
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ser Glu Val Ser Leu
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Ala Arg Asp Cys
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Tyr Thr Leu His Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 34

Ile Thr Ala Pro Tyr Ser
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Asn Asp Leu Ser Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Arg Gly Asn Ser Gly
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Arg Lys Ala Ser Val
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Ala Glu Val Phe Met
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ala Ala Gly Leu Asn
1               5

<210> SEQ ID NO 40
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Pro Leu Pro Leu Phe
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Asn Lys Gly Trp Ala
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys His Met Leu Arg Trp
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Gln Arg Leu Gly Lys
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Leu Gln Arg Gly
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Glu Lys Pro Arg Arg
```

-continued

```
1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Leu Val Ser Thr His
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Ala Ser Leu Arg Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Leu His Ala Gly
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Trp Thr Trp Leu Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Thr Leu Gly Phe Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 51

Ile Pro Gly Leu Leu Leu
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Val Cys Leu Leu Thr Val
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Gly Phe Thr Met
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Trp Val Gly Gly Ala
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Ala Met Gln Pro Gly
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Asp Leu Lys Arg Leu
1               5

<210> SEQ ID NO 57

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Arg Asn Ser Met Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Val Cys Asn Lys Thr
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Trp Ser Trp Glu Gln
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Asn Met Ala His Phe
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Phe Asp Ser Phe Cys Arg
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

```
Gln Ala Val Leu Met Gln
1               5
```

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gly Lys His Tyr Gln Trp
1               5
```

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gln Ser Arg Lys Ser Phe
1               5
```

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Tyr Ser Ser Val Asp
1               5
```

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Glu Arg Cys Arg Val Asp
1               5
```

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Tyr Ala Pro Ser Thr Arg
1               5
```

<210> SEQ ID NO 68
<211> LENGTH: 6
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 68

Ser Ile Gly Gln Ser Lys
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Cys Pro Gln Phe Cys
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Gly Gly Leu Gly Leu
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Gly Gly Leu Gly Ile
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Gly Gly Leu Gly Arg
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Gly Gly Leu Asn Val
1               5

```
<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Gly Gly Leu Arg Ala
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Gly Gly Leu Glu Met
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Gly Gly Ile Ala Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Gly Gly Ile Ala Val
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Gly Gly Ile Arg Pro
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

Tyr Gly Gly Trp Ala Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Gly Gly Trp Gly Pro
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Gly Gly Trp Ser Ser
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Gly Gly Met Lys Val
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Gly Gly Phe Pro Asp
1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Tyr Gly Ser Leu Val Leu
1               5

<210> SEQ ID NO 85
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 85

Tyr Gly Ser Leu Val Gln
1               5

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Gly Ser Leu Val Arg
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Gly Ser Leu Ala Asp
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Gly Ser Leu Leu Ser
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Gly Ser Leu Asn Gly
1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Tyr Gly Ser Leu Tyr Glu
1               5
```

```
<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Gly Ser Trp Ala Ser
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Gly Ser Trp Gln Ala
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Gly Ser Phe Leu His
1               5

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Tyr Gly Ala Leu Gly Gly
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Tyr Gly Ala Leu Ser Trp
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 96

Tyr Gly Ala Leu Asp Thr
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Gly Ala Leu Glu Leu
1               5

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Gly Ala Ile Gly Phe
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Gly Ala Trp Thr Arg
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Gly Trp Trp Gly Leu
1               5

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Tyr Gly Trp Trp Leu Thr
1               5

<210> SEQ ID NO 102
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 102

Tyr Gly Trp Leu Ala Thr
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Trp Ala Asn Lys
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Gly Asn Trp Thr Tyr
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Tyr Gly Asn Phe Ala Asp
1               5

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Gly Asn Phe Pro Ala
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Tyr Gly Thr Phe Ile Leu
1               5
```

```
<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Tyr Gly Thr Trp Ser Thr
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Gly Val Trp Ala Ser
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Tyr Gly Val Trp Trp Arg
1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Gly Leu Trp Gln Ser
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Tyr Gly Phe Trp Gly Met
1               5

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 113

Tyr Gly Lys Trp Ser Gly
1               5

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Tyr Gly Pro Phe Trp Ser
1               5

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Gly Glu Phe Val Leu
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Gly Asp Phe Ala Phe
1               5

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Tyr Ala Trp Gly Trp Gly
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Tyr Ala Gly Phe Ala Gln
1               5

<210> SEQ ID NO 119
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Ser Met Phe Lys Glu
1               5

<210> SEQ ID NO 120
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tatgaggttt tgccagacaa ctggaacagt tcagcggag tgccagtaga atggaacaac        60
taaagg                                                                  66

<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggagtgagag taga                                                         14

<210> SEQ ID NO 122
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ctttcaacag t                                                            11

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cgatctaaag ttttgtcgtc t                                                 21

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Gly Gly Phe
1
```

```
<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Gly Gly Phe Leu
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Gly Gly Phe Met
1               5

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Tyr Gly Gly Leu
1

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Gly Phe Leu
1

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Phe Leu
1

<210> SEQ ID NO 130
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (11)..(12)
<223> OTHER INFORMATION: a, c, g or t
<220> FEATURE:
<221> NAME/KEY: modified_base
<222> LOCATION: (14)..(15)
<223> OTHER INFORMATION: a, c, g or t
<220> FEATURE:
<221> NAME/KEY: modified_base
<222> LOCATION: (17)..(18)
<223> OTHER INFORMATION: a, c, g or t
<220> FEATURE:
<221> NAME/KEY: modified_base
<222> LOCATION: (20)..(21)
<223> OTHER INFORMATION: a, c, g or t
<220> FEATURE:
<221> NAME/KEY: modified_base
<222> LOCATION: (23)..(24)
<223> OTHER INFORMATION: a, c, g or t
<220> FEATURE:
<221> NAME/KEY: modified_base
<222> LOCATION: (26)..(27)
<223> OTHER INFORMATION: a, c, g or t

<400> SEQUENCE: 130
ctctcactcc nnknnknnkn nknnknnkgg cggcactgtt gaaagttgt        49

<210> SEQ ID NO 131
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(30)
<220> FEATURE:
<221> NAME/KEY: CDS
<222> LOCATION: (49)..(84)
<220> FEATURE:
<221> NAME/KEY: modified_base
<222> LOCATION: (31)..(32)
<223> OTHER INFORMATION: a, c, g or t
<220> FEATURE:
<221> NAME/KEY: modified_base
<222> LOCATION: (34)..(35)
<223> OTHER INFORMATION: a, c, g or t
<220> FEATURE:
<221> NAME/KEY: modified_base
<222> LOCATION: (37)..(38)
<223> OTHER INFORMATION: a, c, g or t
<220> FEATURE:
<221> NAME/KEY: modified_base
<222> LOCATION: (40)..(41)
<223> OTHER INFORMATION: a, c, g or t
<220> FEATURE:
<221> NAME/KEY: modified_base
<222> LOCATION: (43)..(44)
<223> OTHER INFORMATION: a, c, g or t
<220> FEATURE:
<221> NAME/KEY: modified_base
<222> LOCATION: (46)..(47)
<223> OTHER INFORMATION: a, c, g or t

<400> SEQUENCE: 131 cct tta gtt gtt cca ttc tac tct cac tcc nnknnknnkn nknnknnk ggc    51
Pro Leu Val Val Pro Phe Tyr Ser His Ser                     Gly
1               5                   10 ggc act gtt gaa agt tgt ctg gca aaa cct cat a                      85
Gly Thr Val Glu Ser Cys Leu Ala Lys Pro His
            15                  20
```